United States Patent
Desmulliez et al.

(10) Patent No.: US 10,024,806 B2
(45) Date of Patent: Jul. 17, 2018

(54) MICROWAVE CAVITY SENSOR

(71) Applicant: HERIOT-WATT UNIVERSITY, Edinburgh (GB)

(72) Inventors: Marc Desmulliez, Edinburgh (GB); Sumanth Kumar Pavuluri, Edinburgh (GB); David Flynn, Kinross (GB); David Herd, Auchterarder (GB)

(73) Assignee: HERIOT-WATT UNIVERSITY (GB)

( * ) Notice: Subject to any disclaimer, the term of this patent is extended or adjusted under 35 U.S.C. 154(b) by 644 days.

(21) Appl. No.: 14/397,696

(22) PCT Filed: May 2, 2013

(86) PCT No.: PCT/GB2013/051143
§ 371 (c)(1),
(2) Date: Oct. 29, 2014

(87) PCT Pub. No.: WO2013/164627
PCT Pub. Date: Nov. 7, 2013

(65) Prior Publication Data
US 2015/0097561 A1    Apr. 9, 2015

(30) Foreign Application Priority Data

May 2, 2012    (GB) .................................. 1207714.5

(51) Int. Cl.
*G01N 22/00* (2006.01)
*G01N 24/08* (2006.01)

(52) U.S. Cl.
CPC ............. *G01N 22/00* (2013.01); *G01N 24/08* (2013.01)

(58) Field of Classification Search
CPC .............................. G01N 22/00; G01N 24/00
See application file for complete search history.

(56) References Cited

U.S. PATENT DOCUMENTS

| 4,785,245 | A | 11/1988 | Lew et al. |
| 6,496,018 | B1* | 12/2002 | Nagata ................... G01N 22/00 324/632 |
| 7,190,177 | B2 | 3/2007 | Zoughi et al. |
| 7,898,265 | B2 | 3/2011 | Takeuchi et al. |

(Continued)

FOREIGN PATENT DOCUMENTS

| CN | 102262096 | 11/2011 |
| EP | 1116951 A1 | 7/2001 |

(Continued)

OTHER PUBLICATIONS

Flory C A et al.: "Microwave oscillators incorporating high performance distributed Bragg reflector microwave resonators", IEEE Transactions on Ultrasonics, Ferroelectrics and Frequency Control, IEEE, US, vol. 45, No. 3, May 1998 (May 1998), pp. 824-829, XP011437755.

(Continued)

*Primary Examiner* — Clayton E LaBalle
*Assistant Examiner* — Ruifeng Pu
(74) *Attorney, Agent, or Firm* — Sheridan Ross P.C.

(57) ABSTRACT

A sensor comprising: a dielectric waveguide for guiding a microwave signal; and a dielectric reflector at an end of the dielectric waveguide to cause formation of a sensing field beyond an outer surface of the dielectric reflector.

19 Claims, 9 Drawing Sheets

(56) References Cited

U.S. PATENT DOCUMENTS

| | | | |
|---|---|---|---|
| 2007/0201796 A1* | 8/2007 | Gulde | G02B 6/12007 385/39 |
| 2012/0074936 A1 | 3/2012 | Kayano | |
| 2013/0014594 A1* | 1/2013 | Neumann | G01F 1/86 73/861.71 |

FOREIGN PATENT DOCUMENTS

| | | |
|---|---|---|
| EP | 1895290 A1 | 3/2008 |
| GB | 1366235 A | 9/1974 |
| JP | 2002189070 A | 7/2002 |
| JP | 2012026769 A | 2/2012 |
| WO | WO 00/28615 A1 | 5/2000 |

OTHER PUBLICATIONS

Search Report prepared by the U.K. Patent Office dated Aug. 21, 2012, for Application No. GB1207714.5.

Sinclair K I et al.: "Open Ended Microwave Oven for Packaging"; ISBN: 978-2-35500-006-5, DTIP of MEMS & MOEMS Apr. 9-11, 2008.

Baba T. et al.: "A Novel Short-Cavity Laser with Deep-Grating Distributed Bragg Reflectors"; Jpn. J. appl. Phys. vol. 35 (1996) pp. 1390-1394, Part 1, No. 2B, Feb. 1996.

Venkatesh M.S. et al.: "An overview of dielectric properties measuring techniques"; Canadian Biosystems Engineering, vol. 47, No. 7, 2005, pp. 15-30.

International Search Report prepared by the European Patent Office dated Jul. 11, 2013, for International Application No. PCT/GB2013/051143.

Krause H-J et al.: "Dielectric microwave resonator for non-destructive evaluation of moisture and salinity", $9^{th}$ European Conference on NDT: ECNDT Berlin 2006; Sep. 25-29, 2006, European Federation for Non-Destructive Testing, Berlin, Sep. 29, 2006 (Sep. 29, 2006), pp. 1-12, XP008104806.

Udo Kaatze: "Techniques for measuring the microwave dielectric properties of materials", Metrologia, Institute of Physics Publishing, Bristol, GB, vol. 47, No. 2, Mar. 8, 2010 (Mar. 8, 2010), pp. S91-S113, XPO20171416.

M.S. Venkatesh et al.: "Microwave oscillators incorporating high performance distributed Bragg reflector microwave resonators", IEEE Transactions on Ultrasonics, Ferroelectrics and Frequency Control, IEEE, US, vol. 45, No. 3, May 1998 (May 1998), pp. 824-829, XP011437755.

Official Action and Search Report with English Translation for China Patent Application No. 201380035643.3, dated 2016, 9 pages.

* cited by examiner

MICROWAVE CAVITY SENSOR

CROSS REFERENCE TO RELATED APPLICATIONS

This application is a national stage application under 35 U.S.C. 371 and claims the benefit of PCT Application No. PCT/GB2013/051143 having an international filing date of May 2, 2013, which designated the United States, which PCT application claimed the benefit of Great Britain Application No. 1207714.5 filed May 2, 2012, the disclosures of both the above-identified applications are incorporated herein by reference.

INTRODUCTION

The present invention relates to a microwave cavity sensor. The microwave cavity sensor of the invention is particularly useful for the detection of the composition of a multiphase mixture, the measurement of corrosion and the determination of the chemistry of dielectric materials, the latter when used in conjunction with Electron Paramagnetic Resonance (EPR) and Nuclear Magnetic Resonance (NMR).

BACKGROUND

Monitoring of pipes and canalisations in the oil and gas industry requires a large number of measurements to be performed in order to control or prevent the development of scale and corrosion or for managing and monitoring a fluid flow when the fluid has to be transported a long distance in a pipeline. The composition and the flow rates of individual components of a mixture of oil and water and possibly gas fluid flowing in a pipe need to be monitored. These measurements are needed to determine the constituents present in the oil well and also to help control and maximise oil extraction.

Conventional techniques for measuring composition and flow rates of individual components require separate measurement of the flow of each of the fluid components. Alternatively, multiphase meters can be used to measure the composition and the flow rates without prior separation. These meters measure the flow speed and the relative fractions of the oil, water and gas (it may also need the temperature, pressure, density of the oil and gas, and the water salinity as input parameters for compensational purposes). The space available for a multiphase meter in an off shore Christmas tree production system is limited. Therefore, there is a need for a compact multiphase meter.

Corrosion monitoring is another significant problem, particularly in the oil and gas industry. The aggressive influence of acids, alkaline solutions and gases cause corrosion in metals. Corrosion in plastics is caused due to the capture of foreign particles, UV light and heat. Both corrosion mechanisms can be monitored, inspected and tested by optimised sensor probes that operate at microwave or high frequency part of the electromagnetic spectrum.

The most widely used techniques for corrosion detection and monitoring in oil and gas pipelines are the Electrical Resistance (ER) monitoring and weight loss coupons. These methods detect metal loss. They fail to detect deterioration in paint or protective coating materials and the conditions responsible for the onset of corrosion. Non-Destructive Testing (NDT) techniques such as ultrasonics, radiography, thermography and eddy current measurement techniques are not sensitive enough for corrosion prognostics. Furthermore, paint, primer and corrosion products are typically dielectric (insulating) materials. Therefore, these methods are unsuitable for detecting and evaluating properties (i.e. presence and thickness) of corrosion layers under thin layers of paint and primer.

Corrosion of metal is a complex problem and its effect on commercial and industrial equipment is immense for the safety and integrity of a large array of assets. A better predictability of corrosion growth under insulation through the early detection of corrosion is needed. Recent results in near-field microwave non-destructive inspection techniques for detecting corrosion under paint and primer in aluminium panels are indicative of the potential advantages of using microwave signals. For example, U.S. Pat. No. 7,190,177 describes a microwave sensor for sensing rust under paint and composite. The sensor can be used for imaging the corrosion of materials depending on a measurement of phase shift of a reflected signal. The sensor can also determine the level of the bulk material from the propagation time of the pulse. However, the sensor cannot detect dielectric or material properties, and so cannot detect changes in these properties.

To simulate reservoir oil, measurements systems of properties of the formation rock such as porosity, permeability and fluid saturation are needed. Until recently, core samples were the only source of permeability. In addition, data collected from the reservoirs can be sparse and expensive to obtain. Nuclear Magnetic Resonance (NMR) data can be a valuable tool for collecting the permeability-porosity data. For example, U.S. Pat. No. 4,785,245 describes a NMR well logging tool used by the oil industry to determine, in situ, the porosity and permeability of fluid-rocks. Particularly for permeability determination, NMR is better than other well logging methods because the NMR signal relaxation times (T1 or T2) can be used to provide information about pore size distributions. NMR also provides a measure of the total hydrogen based in the rocks. Other studies show that another magnetic resonance technique—Electron Paramagnetic Resonance (EPR)—produces a detectable signal from organic-free radicals in crude oils, but not from water or from gas. The amplitudes of these EPR signals are proportional to the amount of oil inside the rock and should, therefore, directly measure the oil fraction in fluid-rocks or the oil fraction of the crude oil mixture. When used with NMR, this method can thus allow the detection of the components of water and oil in the rocks (and possibly the gas) separately.

EPR spectrometers in general detect the concentration and composition of free radicals in a sample. The sample is usually loaded into a high-frequency resonant cavity in a slowly varying uniform magnetic field. Unpaired electrons irradiated with microwave radiation at a fixed frequency undergo resonant transitions between the spin-up and spin down state at a characteristic magnetic field. The energy difference between these two energy levels is called the Zeeman splitting. For an electron in free space, the Zeeman splitting is equal to $h\nu = g\beta H$ where $\nu$ is the excitation frequency, H is the applied magnetic field, $\beta$ is the Bohr magneton, h is Planck's constant, and g is a factor that depends on the molecule.

Most EPR measurements are made with microwaves in the 9000-10000 MHz (9-10 GHz) region with magnetic field intensities corresponding to about 3500 Gauss (0.35 T). For example, for the field of 3350 Gauss, electron spin resonance occurs near 9400 MHz (EPR) for an electron compared to only about 14.3 MHz (NMR) for nuclear magnetic resonance. Many EPR spectroscopy systems have difficulty with automatic frequency control (AFC) locking to a low Q resonator. This difficulty is more commonly experienced at low powers of less than −70 dbm. Difficulty in obtaining an AFC lock may cause frequency drift, error voltage, dispersion and noise. A higher Q system makes it easier to obtain a frequency lock without GaAs FET amplifications. Therefore, there is a need for an EPR probe having a high Q.

SUMMARY OF THE INVENTION

According to the present invention, there is provided a sensor for sensing a sample using a microwave signal at an excitation wavelength, the sensor comprising: a dielectric waveguide for guiding the microwave signal; and a dielectric reflector at an end of the dielectric waveguide to cause formation of a sensing field beyond an outer surface of the dielectric reflector. Alternatively, the dielectric reflector can cause a sensing field just beneath the inner surface of the dielectric reflector. In this case, the material to be sensed is placed just beneath the inner surface of the dielectric reflector or if necessary in a recess machined within the dielectric reflector. In this case, the recess lateral dimensions can be from 1 mm×1 mm and up to the lateral dimensions of the dielectric reflector. The recess thickness can be up to the thickness of the dielectric reflector.

The dielectric waveguide may be arranged to allow formation of a standing wave at the excitation wavelength within the waveguide. The standing wave may be resonant at half the excitation wavelength. The sensing field may be an evanescent field or a radiating field.

The sensor may include a concentrator arranged around the waveguide for concentrating microwave energy in the waveguide. The concentrator may be a distributed Bragg reflector structure. The Bragg reflector structure may be a honey comb structure.

BRIEF DESCRIPTION OF THE DRAWINGS

Various aspects of the invention will now be described by way of example only and with reference to the accompanying drawings, of which:

FIG. 11 (b) is a close up view of FIG. 11 (a). Resonator Q factor is ~100000;

DETAILED DESCRIPTION OF THE INVENTION

Figure 1:
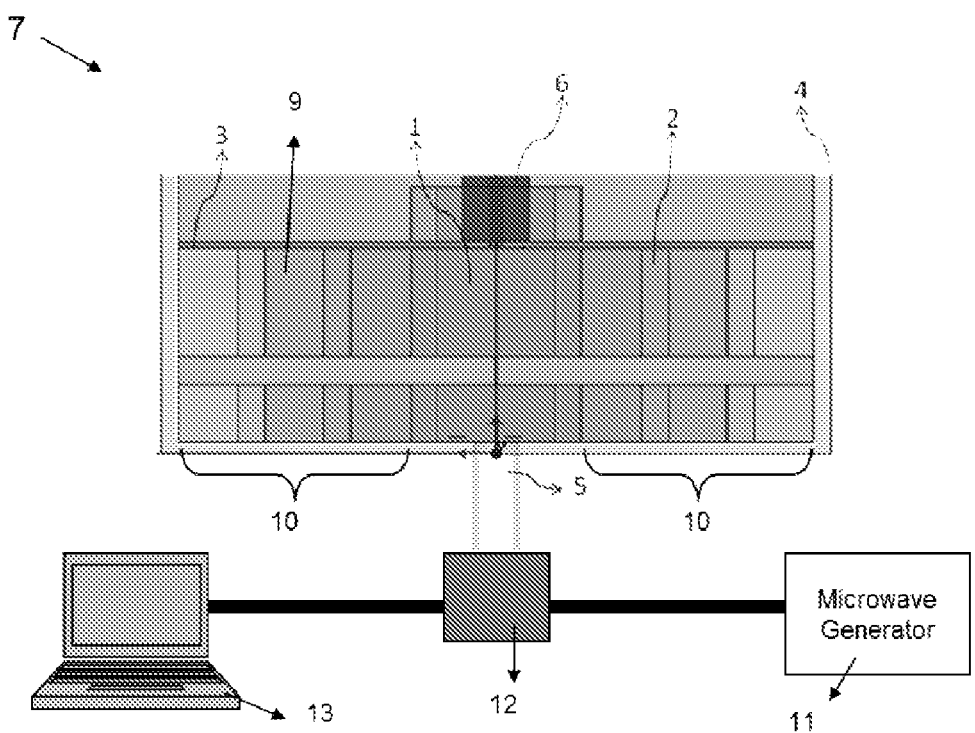
FIG. 1 is a vertical cross-section of a high Q Bragg reflector based open ended microwave resonator sensor.

FIG. 1 shows a cross section of a high Q Bragg reflector based open ended microwave resonator sensor 7. The sensor 7 is dielectric structure having a waveguide 1 and a concentrator 10 surrounding the waveguide 1. One end of the waveguide is connected to a microwave generator 11 via a SMA connector 5, so that microwaves can be injected along a longitudinal axis of the waveguide. The opposite end along the longitudinal axis of the waveguide is terminated with a dielectric reflector 3 of defined thickness. The waveguide 1 extends beyond the dielectric reflector to form a sample chamber 6. The waveguide 1 has a resonant wavelength of half the excitation wavelength $\lambda/2$. The dielectric reflector has a thickness of at least $\lambda_g/20$ where $\lambda_g$ is the wavelength of the excited electromagnetic wave in the dielectric. The function of the dielectric reflector is to maximise electromagnetic field intensity in the sample chamber 6. In practice, the dielectric reflector should be made of a dielectric material that is different to that of the dielectric waveguide.

The concentrator 10 has an array of cavities. In the example shown in FIG. 1, the array comprises a plurality of cavities resonant at $\lambda/2$ and a plurality of cavities resonant at $\lambda/4$. However, other cavity arrangements could be used, for example, an array of $\lambda/8$ cavities or cavities that are an odd multiple of $\lambda$. The waveguide 1 is separated from the concentrator cavities 9 by dielectric reflectors 2 of thickness $\lambda/4$. A number of different structures can be implemented. For example, the $\lambda/4$ cavities 9 can be arranged in a honey comb fashion with the central slot taken up by the $\lambda/2$ resonator. The waveguide 1, concentrator 10 and the dielectric reflector 3 are in a hollow metallic housing 4. In use, microwave signals are injected into and the measurement field sensed from the same end of the waveguide 1.

The waveguide has a cross-section that supports waveguide modes that constitute a dominant standing electromagnetic wave between the reflector 3 and the bottom layer of the hollow metallic housing 4 with the intensity of the standing wave stronger just at the vicinity (above and below) of the reflector. Resonance occurs for one of the modes when the length of the resonator corresponds to an integer number of half mode wavelengths between the top reflector 3 and the bottom layer of the hollow metallic housing 4.

When an electromagnetic field is excited at the resonance frequency of $\lambda/2$, standing waves form along a longitudinal axis of the $\lambda/2$ resonator waveguide 1. The confinement of the standing waves and the electromagnetic field maxima increases the Q factor of the microwave resonator. Using dielectric walls to form the resonator increases the Q factor as these have only minimal dielectric losses (the loss tangent of the dielectric wall material is close to zero). The field maximum is controlled at the surface of the sensor by controlling the thickness of dielectric reflector.

The sensor can be used for sensing different types of samples such as gas, liquids, solids or a combination of the three and within the sample determining the presence and concentration of a specific compound. The sensor can operate in a near field mode when excited below a defined cut-off frequency or in a far field mode when excited above the cut-off frequency.

In the near field mode, a very high Q standing wave pattern is required. For example, for near field operation a Q factor more than ten and ideally more than twenty would be preferred. In this case, there is no intrinsic wave impedance match with the surroundings (air). Instead the sensor is operated below cut off when compared with the resonant frequency of the dielectric waveguide, for example $TM_{111}$ mode, thereby producing an evanescent wave constituting a near field in the sensing region. This means that the sensing region 6 is operated below cut off when compared to resonant frequency of waveguide region 1. To achieve this, the lateral dimensions of region 6 have to be selected such that the resonance frequency is below the resonance frequency of region 1.

In the near field mode, a standing wave is formed by total internal reflection at the interface with the dielectric reflector 3. An evanescent wave is formed that extends into the sample chamber 6. Changes in the field in the sample chamber 6 are indicative of the presence of a sample, and can be used to determine sample characteristics. When operated in the near field mode the sensor can sense dielectric parameters, such as the shift in resonant frequency (frequency perturbation), the magnitude of the reflected signal and the Q factor of the sensor.

Figure 2:
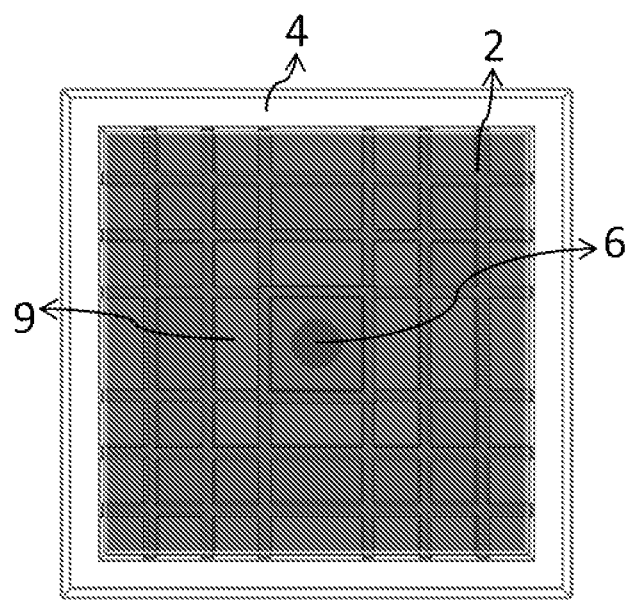
FIG. 2 is a horizontal cross-section of a high Q Bragg reflector based open ended microwave resonator sensor.
Figure 3:
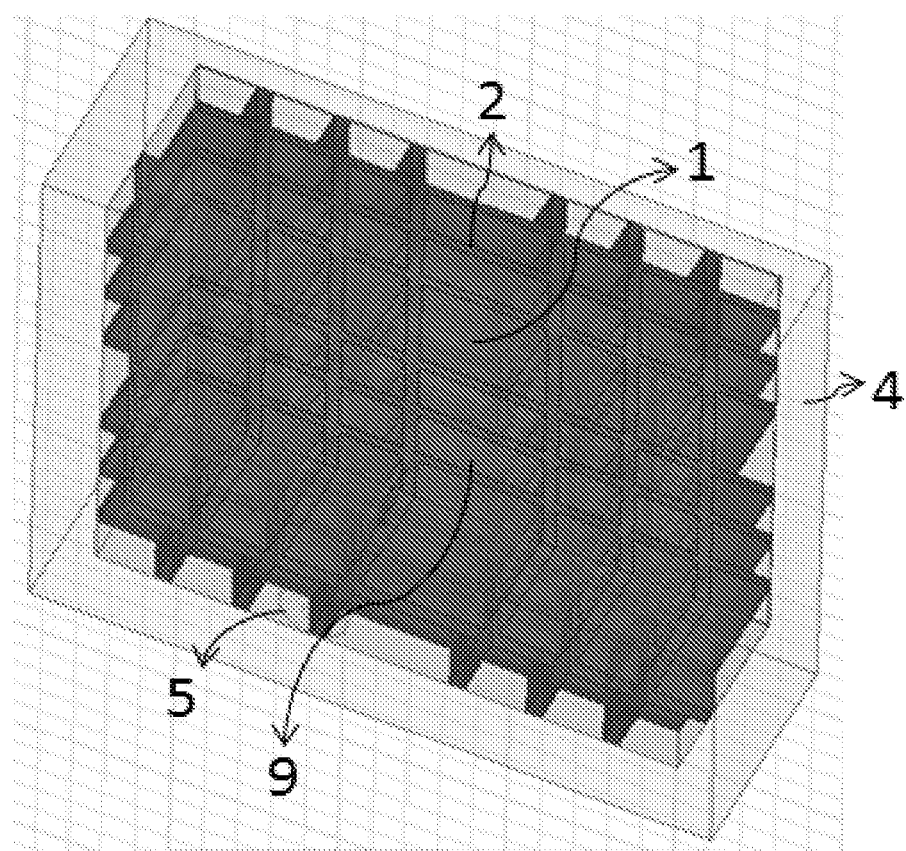
FIG. 3 is a 3D view of the high Q Bragg reflector based open ended microwave resonator of FIG. 1.

In the far field mode, a low Q resonator is sufficient to radiate electromagnetic waves at least 2 cm from the open end surface of the resonator. To achieve far field sensing, ideally the Q factor is less than 10. In this case, there is intrinsic wave impedance match with the surroundings (air and materials to be sensed). To achieve this, the sensor is operated above cut off when compared to the resonant frequency inside the dielectric waveguide. This maintains propagating modes. This means that sensing region 6 is operated above cut off when compared to the resonant frequency of waveguide region 1. Region 6 is maintained above cut off by appropriate selection of the cross-sectional dimensions (the top view of region 6 shown in FIG. 2). In practice, the concentrator 10 shown in FIG. 1 is not required to operate the sensor in the far field mode. Alternatively, the sensor of FIG. 1 could be fed with a signal in a radiating low Q mode.

In the far field mode, the field of the excitation wavelength radiates beyond the dielectric reflector surface. In this case the sample is at a distance that can range between 0.1 mm to 100 cm from the sensor. When the sensor is operated in the far field mode reflected signal parameters, such as the backscattering (diffuse reflection), specular reflection of the transmitting signal, the time difference between the transmitted and reflected signal and the magnitude of the backscattered or specular reflection of the transmitted signal can be measured.

Figure 4:
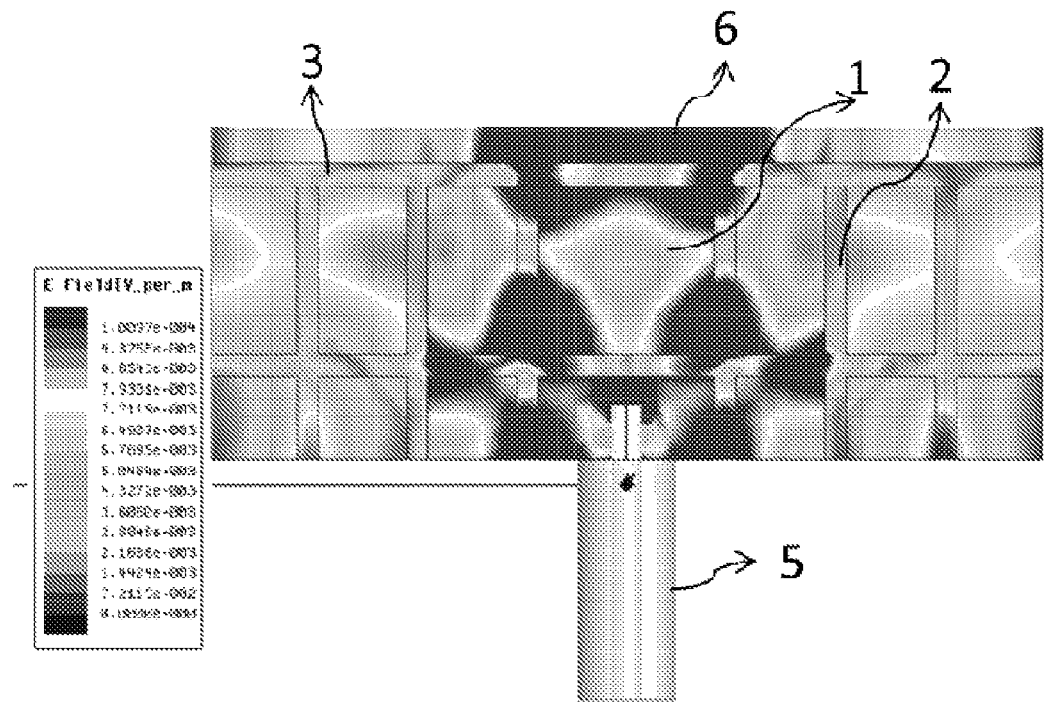
FIG. 4 is a simulated standing wave electromagnetic field distribution in the high Q Bragg reflector based open ended microwave resonator showing the effect of the dielectric reflector 3.
Figure 5:
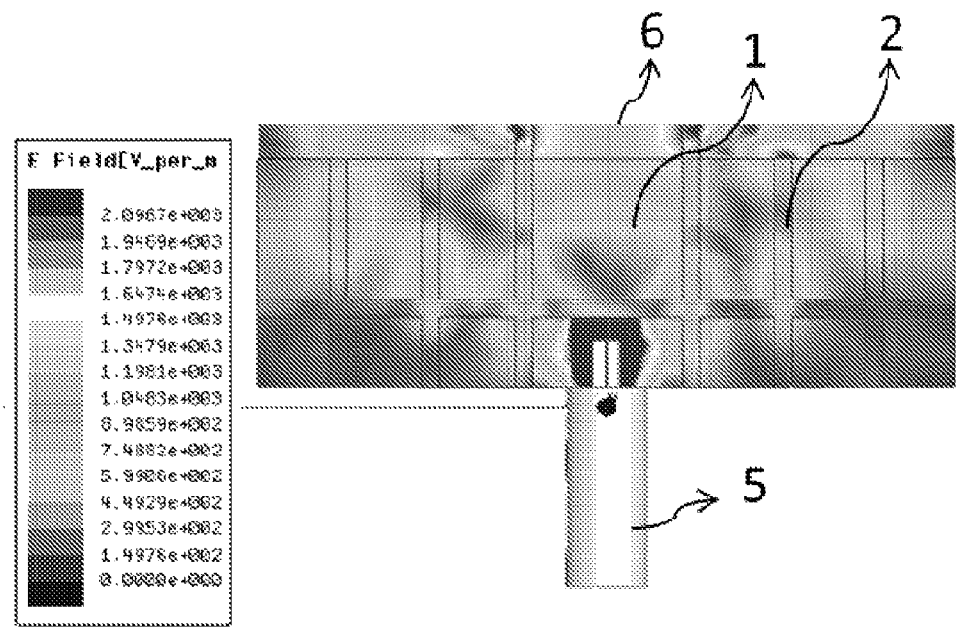
FIG. 5 is a simulated standing wave electromagnetic field distribution in the high Q Bragg reflector based open ended microwave resonator without the dielectric reflector 3.

FIG. 4 shows a simulated standing wave electromagnetic field distribution in the high Q Bragg reflector based open ended microwave resonator of FIG. 1. This shows that the electromagnetic field intensity is maximised (darkest colour) at the surface of the dielectric reflector of the sensor. High intensities of electric field can also be observed just below the surface of the dielectric reflector, as the material in this area constitutes air with a relative dielectric constant of 1, whereas the surface of the sensor has a relative dielectric constant of 10. For comparison, FIG. 5 shows a simulated standing wave electromagnetic field distribution in the resonator of FIG. 1 when the dielectric reflector is removed. In this case, the field in the sample region 6 is relatively low when compared with that of FIG. 4. This demonstrates that the dielectric reflector maximises the sensing field, and so increases sensor sensitivity.

The EM field intensity at the open end of the sensor is controlled by the reflection co-efficient of the dielectric reflector, which is controlled by the thickness and permittivity of the dielectric reflector material. Typically, the permittivity of the dielectric reflector is higher than that of the waveguide dielectric material and is of very low loss material. The thickness of the dielectric reflector may be determined using equations based on boundary conditions that exist at the dielectric reflector-air interface and the open end of the waveguide for a given value of permittivity in order to achieve maximum intensity of the EM fields at dielectric reflector-air interface. Using the dielectric reflector 3 enhances the EM field intensity at the interface between the insert dielectric and the sensing region 6. If a high permittivity dielectric is used to achieve this, the boundary conditions between region 1 and region 2 dictate that the modal field patterns in region 2 will set-up strong non-propagating (evanescent) EM-fields in region 6. These evanescent fields will be a source of sensing mechanism for near field operation. Ceramic, teflon or glass based dielectric materials are suitable examples for dielectric reflectors, although any dielectric material that has a dielectric constant different from that of the dielectric waveguide can be used in principle.

The microwave wave cavity resonator sensor 7 can be used to sense different physical quantities that depend on the complex permittivity or on the complex permeability of a material under test. The sensor principle is based on the change in resonant frequency of the microwave cavity when a dielectric material is introduced inside the cavity. The shift in resonant frequency measured from the reflected signal depends on the quality factor of the microwave resonator cavity and also on the permittivity of the sample, volume of the sample and its position inside the cavity resonator with respect to the intensity of electric field distribution. Thus, the sensor needs to be designed for particular applications as the high sensitivity and resolution depends on the material (to be sensed) characteristics.

The sensor of the invention can be operated in the microwave frequency range or at frequencies higher than microwave. In this case the sensor can be used for "imaging" materials by measuring the change in phase of the reflected signal. Thus, all of the properties of a reflected electromagnetic signal such as the amplitude, the shift in resonant frequency and change in phase are also measurable quantities. The restriction of the electro-magnetic signals to the microwavemillimetre wave part of the spectrum allows a combination of greater penetration of signal and higher sensitivity for the sensors.

Figure 6:
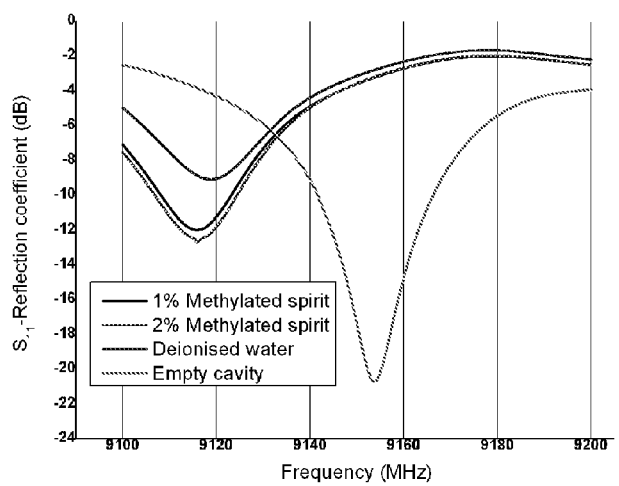
FIG. 6 is a measured frequency response showing frequency perturbation observed (signatures) when different materials are filled in the open ended cavity with a simple open ended microwave resonator with Q factor~1000.

FIG. 6 shows a frequency response obtained when measuring different concentrations of Methylated spirit solutions using an open ended microwave resonator (with Q factor~1000, input frequency in the region of 9155 MHz, input power in the region of −10 dBm). The y axis shows the $S_{11}$ parameter which is the reflection coefficient expressed in dB. Alternatively, it can be expressed in magnitude and also be reversed in magnitude. In this case, the sensor used was the same as that shown in FIG. 1, but without the concentrator. Deionised water and methylated spirit solutions have a characteristic frequency shift of 35 MHz and 40 MHz respectively compared to the frequency measured with an empty cavity. This frequency shift is specific to a particular compound. The amplitude of the frequency response of methylated spirit solution increases with increased concentration of metehylated spirit showing the possibility of not only identifying the presence of specific compound in a liquid, but also measuring their actual concentration.

Figure 7:
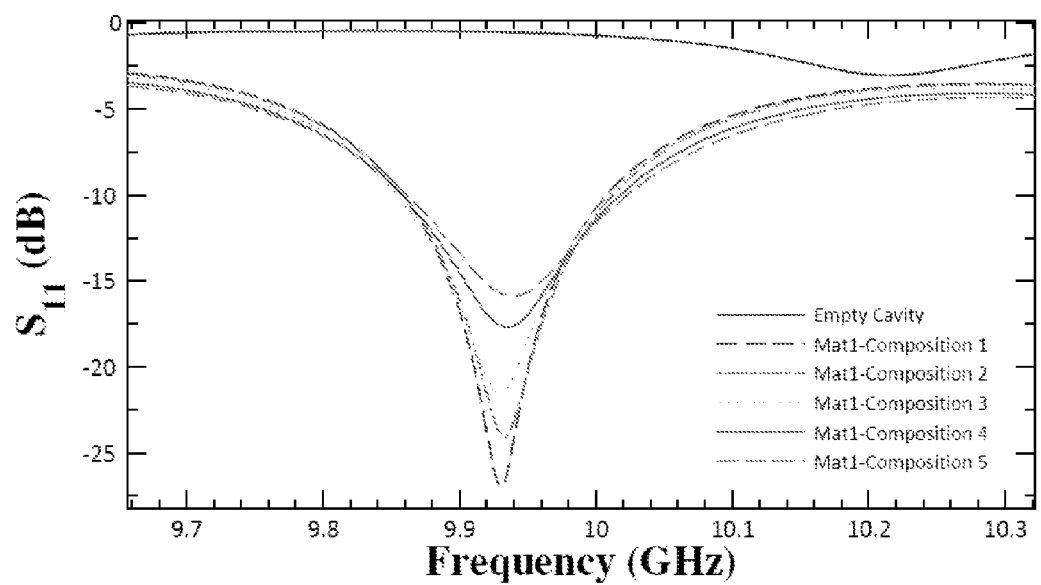
FIG. 7 is a measured frequency response showing frequency perturbation observed (signatures) when different food material percentage composition of Materials 1 are filled in the open ended cavity with a simple open ended microwave resonator with loaded Q factor~600.

FIG. 7 shows a measured frequency response obtained when measuring different compositions of a food product with materials) and with various percentage composition of these materials) using an open ended microwave resonator (with Q factor~1000, input frequency in the range of 9900 MHz, input power in the range of −10 dBm). In this case, the sensor used was the same as that shown in FIG. 1, but without the concentrator. Materials) for instance has a varied percentage composition of skimmed milk, double cream, butter, water (<10%), sugar, modified starch, stabilisers, emulsifier. The materials show a characteristic frequency shift in the range of 200 MHz and 260 MHz respectively compared to the frequency measured with an empty cavity. This frequency shift is specific to a particular composition of materials 1.

Figure 8:
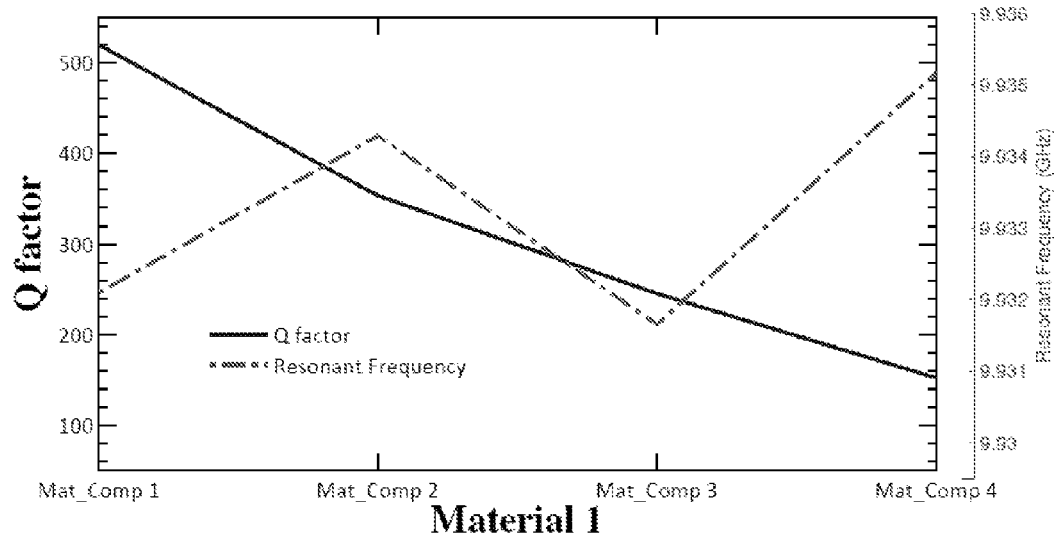
FIG. 8 is a measured resonant frequency response and loaded Q factor showing resonant frequency and Q factor values observed (signatures) when different food material percentage composition of Materials 1 are filled in the open ended cavity with a simple open ended microwave resonator.

FIG. 8 shows resonant frequency and Q factor values observed (signatures) derived for the measurements in FIG. 7 when different food material percentage compositions from composition 1 to composition 4 of materials 1 (shown in FIG. 7) are filled in the open ended cavity with a simple open ended microwave resonator. The measured Q factor response of various compositions of materials 1 shows a definitive shift in Q factor between each of materials 1 compositions as compared with the resonant frequency response. A computer algorithm could be developed take into account the measured reflection parameter magnitude as shown in FIG. 7, resonant frequency and Q factor of the material compositions in order to classify them.

Figure 9:
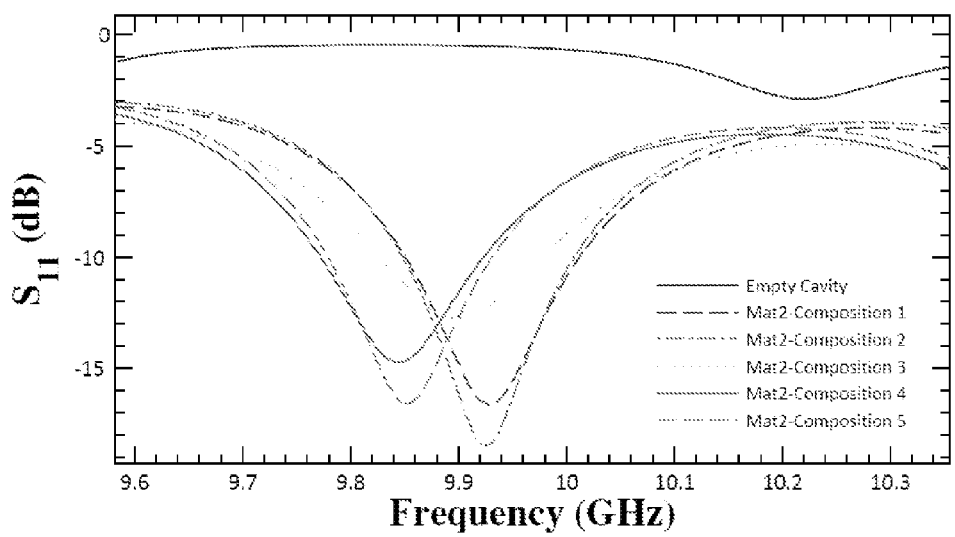
FIG. 9 is a measured frequency response showing frequency perturbation observed (signatures) when different food material percentage composition of Materials 2 are filled in the open ended cavity with a simple open ended microwave resonator with loaded Q factor~600.

FIG. 9 shows a measured frequency response obtained when measuring different compositions of a food product with materials 2 and with various percentage composition of these materials 1 using an open ended microwave resonator (with Q factor~1000, input frequency in the range of 9900 MHz, input power in the range of −10 dBm). In this case, the sensor used was the same as that shown in FIG. 1, but without the concentrator. Materials 2 has a varied percentage composition of skimmed milk, double cream, butter, water (<10%), sugar, modified starch, stabilisers, emulsifier. The materials show a characteristic frequency shift in the range of 300 MHz and 350 MHz respectively compared to the frequency measured with an empty cavity. This frequency shift is specific to a particular composition of materials 2.

Figure 10:
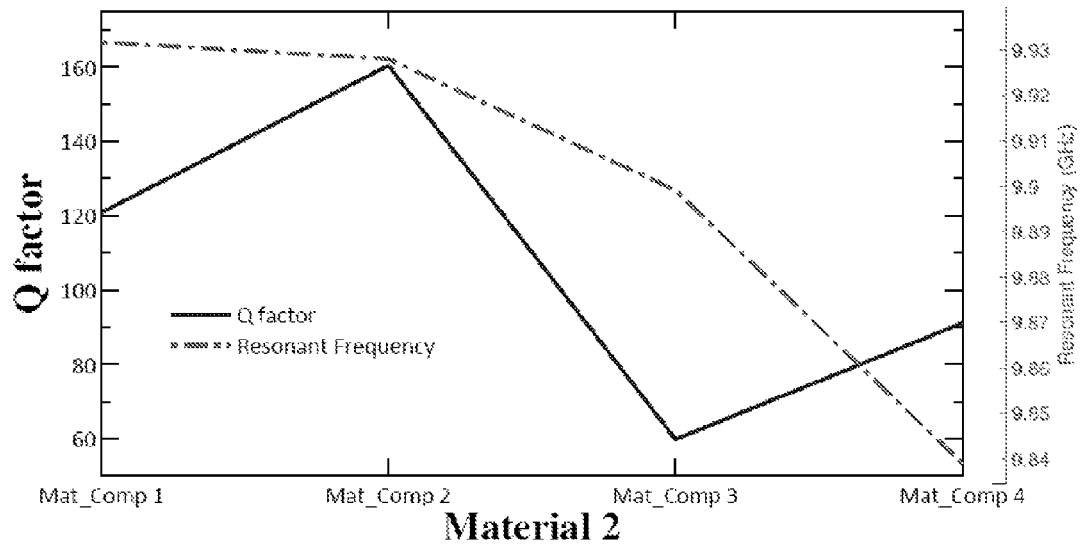
FIG. 10 is a measured resonant frequency response and loaded Q factor showing resonant frequency and Q factor values observed (signatures) when different food material percentage composition of Materials 2 are filled in the open ended cavity with a simple open ended microwave resonator.

FIG. 10 shows resonant frequency and Q factor values observed (signatures) derived for the measurements in FIG. 9 when different food material percentage compositions from composition 1 to composition 4 (shown in FIG. 9) of materials 2 are filled in the open ended cavity with a simple open ended microwave resonator. The measured response of various compositions of materials 2 shows a definitive shift in resonant frequency between each of materials 2 compositions as compared with the loaded Q factor which is smaller shift for these materials 2. Nevertheless, thus, one could develop a computer algorithm which could take into account the measured reflection parameter magnitude as shown in FIG. 9, resonant frequency and Q factor of the material compositions in order to classify them.

Figure 11:
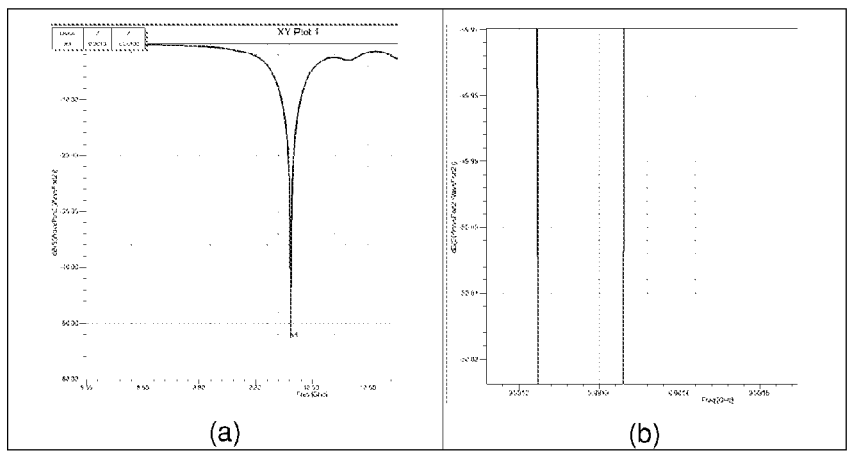
FIG. 11 (a) is a simulation frequency response for the high Q Bragg reflector based open ended microwave resonator shown in FIG. 1.

FIG. 11 shows the simulation frequency response for the high Q Bragg reflector based open ended microwave resonator with a Q factor of ~100000. This indicates that the microwave sensor can be used to accurately distinguish different signatures for various liquid compositions. The simulation is carried out with a commercial finite element method (FEM) based electromagnetic software. The parameters of the simulation are the geometry and dimensions of the high Q Bragg reflector and an input power of 1 W. The output of the software program is the resonant frequency of the resonator along with the Q factor of the resonator. The difference in the simulation of the Q factors shown in FIG. 6 and FIG. 11 is primarily attributed to the concentrator 10 that comprises a honey comb shaped Bragg concentrator. FIG. 6 is generated without the concentrator 10.

The high Q Bragg reflector based open ended microwave resonator described above can be used in a variety of applications. For example, as described above, it can be used as a simple composition sensor. In this case, a liquid composite material of interest is put in the sample region 6 and the liquid composition ratios measured or determined by sensing changes in the sensing field. Other applications include continuous flow rate and composition determination for oil pipes, and corrosion inspection, thickness monitoring of pipes, surfaces etc.

Figure 12:
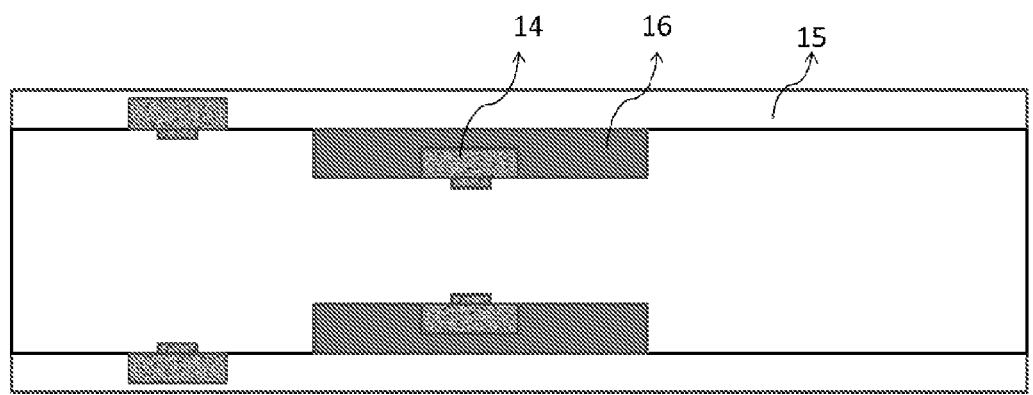
FIG. 12 is a longitudinal cross-sectional view of the main components of the instrumentation that utilizes electromagnetic parameters arranged including the high Q Bragg reflector based open ended microwave resonator in a pipeline for measuring multiphase flow.
Figure 13:
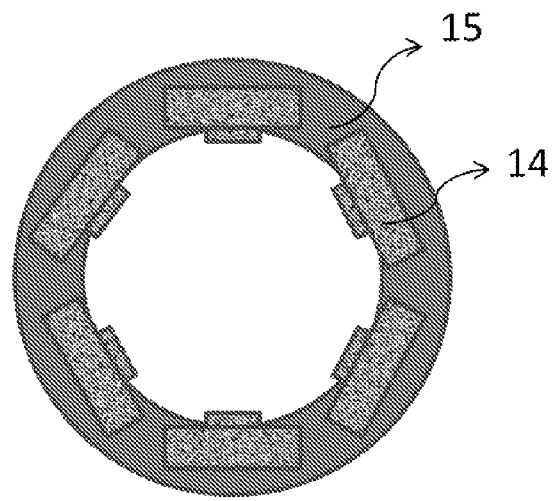
FIG. 13 is a transverse cross-sectional view of the main components of the instrumentation that utilizes electromagnetic parameters arranged including the high Q Bragg reflector based open ended microwave resonator in a pipeline for measuring multiphase flow.

FIG. 12 and FIG. 13 show a system for measuring the composition of a wet gas mixture flowing in a pipeline 15. The system has a plurality of high Q Bragg reflector based open ended microwave resonators mounted on an internal surface of the pipeline, so that the sample chamber of each of the sensors opens into the interior of the pipeline. The sensors are positioned in two regions of the pipeline. The first region has a larger inner diameter than the second region 16 to allow for differential pressure measurements.

A microwave generator is provided (not shown) to generate an excitation signal. The generator can be used to cause an electromagnetic resonance in the sensor causing a controlled fringing electromagnetic field with field maximum adjacent to the surface facing the wet gas flow. Alternatively, the sensor can be excited in non resonance mode and the phase and reflection parameters associated with the sensor recorded. A recording unit coupled to the sensor is adapted to measure the reflection and phase properties; including the reflection magnitude; and derive the resonance Q factor, transmission Q factor and phase difference while the wet gas flow moves past the sensor. A processing unit is provided for digital data analysis that uses principal component and spectral analysis of the resonance and transmission data to estimate a property of at least a part of said wet gas flow.

In use, when the composition is, for example, a mix of oil and water, the amount of oil can be obtained by measuring a frequency perturbation due to the change of equivalent dielectric constant of the whole mixture, the resulting change in Q factor, phase and reflection amplitude at a first frequency spectrum, where the system responds to the very near or fringing electromagnetic fields, and than re-measuring the parameters again at another higher frequency spectrum where the system responds to the far field electromagnetic fields. Once these parameters are measured, data is sent to the processing unit and analysed using PCA and spectral angle techniques to obtain flow composition parameters of the mixture.

In another embodiment, multiphase flow measurement is performed by combining electromagnetic and NMR techniques. The system shown FIGS. 14 and 15 has a strong magnet positioned adjacent to the pipe 15 with a strong constant magnetic field oriented (say >0.1 Tesla) in one direction through the pipe 15. An electromagnetic coil 18 may also be positioned adjacent the container in the vicinity of the constant magnetic field for providing an additional low intensity alternating electro-magnetic field (say 35 dBm to −60 dBm) with the magnetic field oriented in a perpendicular direction to the magnetic field due to the strong magnet. Another electromagnetic coil 15 is placed inside the pipeline for detecting RF emissions from a mixture in the container exposed to these magnetic fields. The high Q open ended Bragg reflector sensor in the near field mode can operate as an EPR spectrometer.

Figure 14:
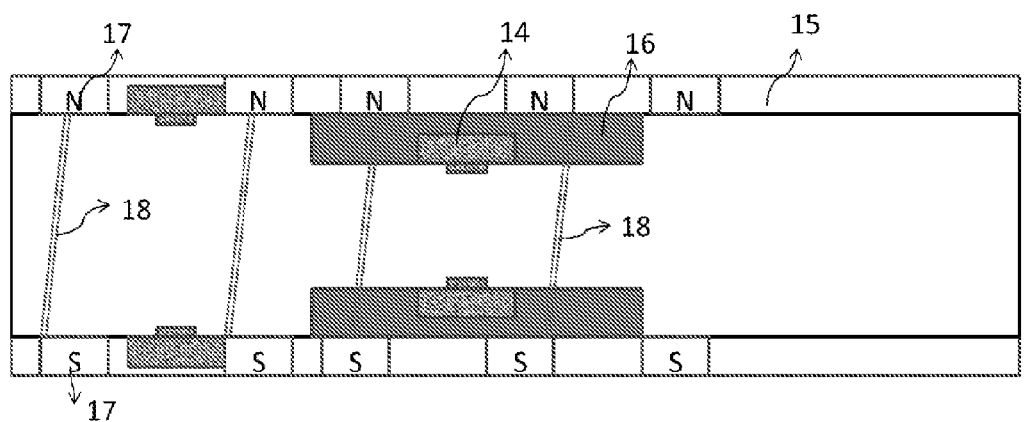
FIG. 14 is a longitudinal cross-sectional view of the main components of the instrumentation that utilizes electromagnetic parameters and NMR parameters arranged including the high Q Bragg reflector based open ended microwave resonator in a pipeline for measuring multiphase flow.
Figure 15:
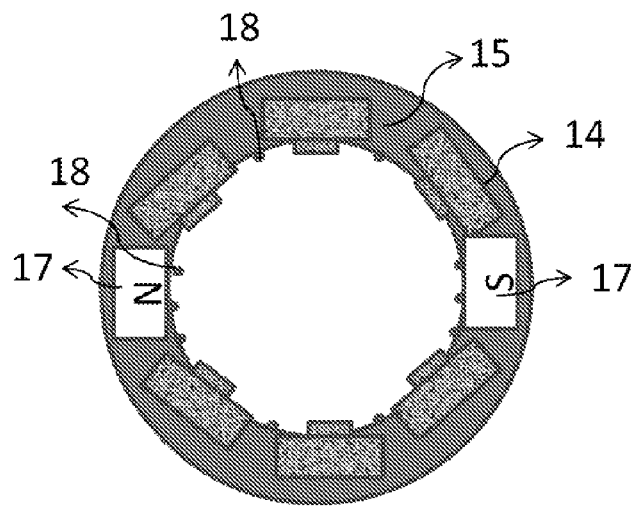
FIG. 15 is a transverse cross-sectional view of the main components of the instrumentation that utilizes electromagnetic parameters and NMR parameters arranged including the high Q Bragg reflector based open ended microwave resonator in a pipeline for measuring multiphase flow.

Using the system of FIGS. 14 and 15 allows an estimate of multiphase flow using EPRNMR and the microwave sensor of the present invention. In a multiphase gas flow which flows undisturbed, the most of the fluid will travel as a film on the pipe wall in a considerable range of conditions. Thus, by using a surface sensitive resonator sensor as described in the present disclosure, a higher sensitivity to fluid content is possible, when measuring the amount and/or composition of the fluid (water/oil/condensate mixture). Combining the NMR, microwave resonance and transmission measurements in a multi phase integrated meter improves sensitivity and accuracy. NMR techniques are known in the art and so will not be described in detail.

Figure 16:
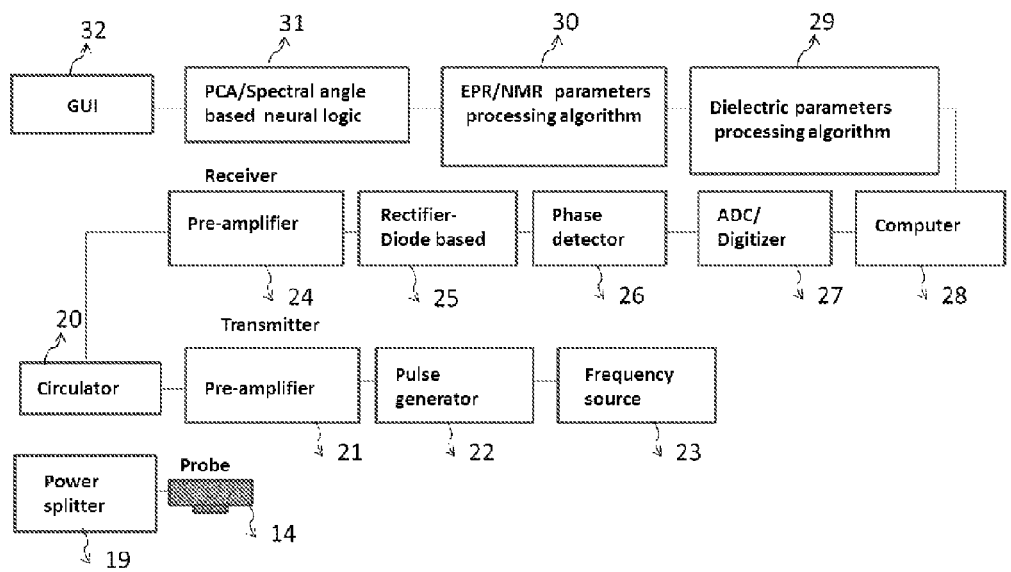
FIG. 16 is a block diagram showing the primary blocks necessary to extract dielectric parameters including the Q factor, the electron paramagnetic resonance and nuclear magnetic resonance parameters for the materials of interest using the high Q Bragg reflector based open ended microwave resonator.

FIG. 16 shows a system for obtaining dielectric, EPR and NMR parameters of materials. This has at least one Bragg sensor probe 14 and at least a pair of, permanent magnets embedded on an internal surface of the pipe 15 shown in FIG. 14 and RF coils for NMR measurements. The dielectric parameters and the EPR parameters can be measured using a single Bragg sensor probe by using a circulator to separate the transmitting (probing signal) and receiving (output) of the signals. Circulators are well known in the art and so will not be described in detail.

The Bragg sensor probe is excited by a signal from microwave frequency source 16 after being amplified 21 generally indicated as in FIG. 16. A pulse controller or generator 22 is provided for setting and controlling durations and periods of intermittent pulses inside the Bragg resonator probe 14. The receiver section has a preamplifier 24, an RF microwave rectifier 25, a lock-in amplifier 26, and a digital converter 27. The digital signal fed to a computer 28. The lock-in amplifier is useful for extracting the signal from a high noise environment. The digital data is identified and processed with different digital algorithms for extracting the dielectric properties 29 and EPRNMR parameters 30 for different materials. Another digital algorithm based on the spectral techniques or principal component analysis techniques 31 is used for correlating the signal with a known digital library. These algorithms are known in the art.

Positioned close to the Bragg sensor is a power splitter and a circulator 20. The circulator is used to route outgoing and incoming signals between the bragg sensor, the transmitter and receiver ports shown in FIG. 16. The use of microwave pulses (if required) and a high dynamic range may lead to temporal overlap of the sent and received pulses requiring a circulator. while the power splitter 19 is used to split power between the set of Bragg reflector sensors as shown in FIG. 16.

Blocks 19-30 in FIG. 16 are associated with the Bragg reflector sensor, and are used for measuring the dielectric and EPR parameters. The NMR parameters need to be measured using coils 18 shown in FIG. 14 at a different frequency of the electromagnetic spectrum (usually RF frequencies from 1 MHz to 20 MHz) and thus will have similar separate blocks 16-22 and 28-29 (not shown).

The microwave measurements associated with the dielectric properties measurements, the microwave measurements associated with the EPR measurements and the NMR measurements associated with the RF frequency measurements can be taken essentially independently. The measurements can be used in combination or correlation or independently using the algorithms noted above to extract the required information about the materials to be sensed.

Microwave or capacitive technology can be used to measure the permittivity of the flow. The permittivity of the flow depends on the permittivity of the components and the permittivity of the flow contains information about the mixture composition. The permittivity is especially sensitive to the water content as the dielectric permittivity of water component is relatively higher at ~81 when compared to the other components. Various kinds of densitometers can be used to measure the density of the flow. Gamma radiation of several energy levels can be combined to yield information about the mixture and chemical composition. Cross-correlation techniques or differential pressure measurements over a restriction in the flow can be used to measure the flow speed.

Figure 17:
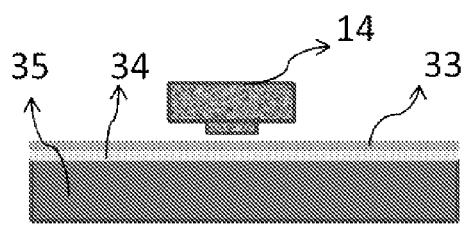
FIG. 17 is a transverse cross-sectional view of the main components of the instrumentation that utilizes near field electromagnetic parameters including the high Q Bragg reflector based open ended microwave resonator for monitoring and inspection of corrosion.

FIG. 17 shows a cross-sectional view of the sensor operating in near field mode for monitoring and inspecting corrosion. The open ended electromagnetic resonant cavity 14 faces towards the walls of a pipeline 35 covered with a protective materials such a paint or elastomers 33 and can be used for monitoring material corrosion 34. The sensors can probe the reflected signal amplitude, change in resonant frequency and reflected signal phase and can deduce the material change as well as change in metal composition due to corrosion 34. Alternatively 34 can be any other dielectric/ metal layer that needs to be detected such as air due to a crack, change in material composition or even thickness of a particular material. The sensor can also probe the direct environment surrounding the corrosion area, therefore giving potential information regarding the cause of corrosion.

Figure 18:
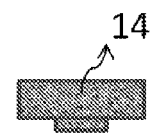
FIG. 18 is a transverse cross-sectional view of the main components of the instrumentation that utilizes far field electromagnetic parameters including the high Q Bragg reflector based open ended microwave resonator for monitoring and inspection of corrosion.
Figure 18:

FIG. 18 shows a cross-sectional view of the sensor operating in the far field mode for monitoring and inspection of corrosion, material faults, cracks etc. The sensor of the invention can be operated frequencies above the microwave range. In this case, the sensor is used for "imaging" the materials by measuring the change in phase of the reflected signal. Thus, all of the properties of a reflected electromagnetic signal such as the amplitude, the shift in resonant frequency and change in phase are also measurable quantities of high precision with these novel probes. The restriction of the electro-magnetic signals to the microwavemillimetre wave part of the spectrum allows a combination of greater penetration of signal and higher sensitivity for the sensors.

Using the sensor of the invention to monitor corrosion allows relatively large asset areas to be monitored more accurately and quicker than existing systems. The sensor can be used for monitoring, inspecting and testing material and metal corrosion on onshore, pipeline, subsea and facilities. To improve sensitivity, the sensor of the invention could be adapted to use microwaves to inductively heat a sample area, and then monitor the cooling rate by monitoring microwave reflection. Since corroded steel cools more slowly than un-corroded steel, this would give a measure of the degree of corrosion.

The open ended electromagnetic resonant cavity 7 can be used independently as a standalone laboratory and hand held configuration as shown in FIG. 1 for detecting the composition of fluids, solid materials, gases enclosed in a chamber in region 6.

Applications for the present invention include, but are not limited to, an affordable, general-purpose bench-top unit for industry, science, or education; an on-line or in-line sensor for petroleum products, lubricants, hydraulic fluids, allowing real-time analysis of critical chemical properties; oxidation, fault detection in the claddings of pipes and composition detection, shelf-life studies for food and drink products; and industry-specific applications, such as for petroleum analysis and as a biomedical detection research tool.

A skilled person will appreciate that variations of the disclosed arrangements are possible without departing from the invention. For example, whilst the sample chamber 6 is shown in the specific embodiments as being at an external surface of the dielectric reflector, it could be just beneath the inner surface of the reflector, where electromagnetic field strength is also higher than in the rest of the waveguide. In this case, the material to be sensed is placed just beneath the inner surface of the dielectric reflector or if necessary in a recess machined within the dielectric reflector. The lateral dimensions of the recess can be from 1 mm×1 mm and up to the lateral dimensions of the dielectric reflector. The recess thickness can be up to the thickness of the dielectric reflector. Accordingly, the above description of the specific embodiment is made by way of example only and not for the purposes of limitation. It will be clear to the skilled person that minor modifications may be made without significant changes to the operation described.

The invention claimed is:

1. A sensor for sensing a sample using a microwave signal at a wavelength of an excited electromagnetic wave, the sensor comprising:

a dielectric waveguide for guiding the microwave signal to allow formation of a standing wave at the wavelength of the excited electromagnetic wave within the dielectric waveguide; and a dielectric reflector at an end of the dielectric waveguide to cause formation of a sensing field beyond an outer surface of the dielectric reflector or below an inner surface of the dielectric reflector, wherein the dielectric reflector comprises a material which has a higher dielectric constant than that of the dielectric waveguide and has a thickness of at least $\lambda_g/20$, where $\lambda_g$ is the wavelength of the excited electromagnetic wave in the dielectric reflector, to thereby maximize electromagnetic field intensity in the sensing field.

2. A sensor as claimed in claim 1, wherein the standing wave is resonant at a fractional multiple of half of the excitation wavelength such as $n\lambda_g/4$, where n is an integer.

3. A sensor as claimed in claim 2, wherein the resonant modes are TM or TE modes.

4. A sensor as claimed in claim 1, wherein the sensing field is an evanescent field.

5. A sensor as claimed in claim 1, wherein the sensing field is a radiating field.

6. A sensor as claimed in claim 1, further comprising a concentrator arranged around the dielectric waveguide for concentrating microwave energy in the dielectric waveguide.

7. A sensor as claimed in claim 6, wherein the concentrator is a distributed Bragg reflector structure.

8. A sensor as claimed in claim 7, wherein the Bragg reflector structure is a honey comb structure.

9. A sensor as claimed in claim 1, wherein the excitation wavelength is in the microwave region between 0.3 GHz to 1 THz.

10. A sensor as claimed in claim 1, further comprising means for detecting change in the sensing field.

11. A sensor as claimed in claim 10, wherein the means for detecting change in the sensing field are operable to measure a frequency difference and/or a phase difference and/or an amplitude difference and/or Q factor difference.

12. A sensor as claimed in claim 10, wherein the means for detecting changes in the sensing field are located at an end of the dielectric waveguide opposite the dielectric reflector.

13. A sensor as claimed in claim 1, further comprising a microwave generator for generating the excitation signal.

14. An electron paramagnetic resonance spectroscope that includes a sensor as claimed in claim 1.

15. A measurement system that includes a sensor as claimed in claim 1 and further comprises a nuclear magnetic resonance system for detecting NMR signals.

16. A measurement system as claimed in claim 15, wherein the sensor and the NMR system are operable to take measurements simultaneously.

17. A sensor as claimed in claim 1, wherein the sensor is a composition sensor, a continuous flow rate and composition sensor, a corrosion inspection sensor, a sensor for monitoring the thickness of pipes or surfaces, a sensor for monitoring the composition of a wet gas mixture flowing in a pipeline, or a sensor for a standalone laboratory and handheld configuration for detecting the composition of fluids, solid materials, gases enclosed in a sample chamber.

18. A sensor for sensing a sample using a microwave signal at an excitation wavelength, the sensor comprising:
- a dielectric waveguide for guiding the microwave signal;
- a dielectric reflector at an end of the dielectric waveguide to cause formation of a sensing field; and
- a concentrator arranged around the dielectric waveguide for concentrating microwave energy in the dielectric waveguide, wherein the concentrator is a distributed Bragg reflector structure.

19. A sensor as claimed in claim 18, wherein the Bragg reflector structure is a honey comb structure.

* * * * *